United States Patent
Hangx et al.

(10) Patent No.: US 10,407,373 B2
(45) Date of Patent: Sep. 10, 2019

(54) PROCESS FOR THE SEPARATION OF FORMIC ACID FROM METHYLTETRAHYDROFURAN

(71) Applicant: Georgia-Pacific LLC, Atlanta, GA (US)

(72) Inventors: Gerardus Wilhelmus Adrianus Hangx, Echt (NL); Gerardus Johannes Paulus Krooshof, Echt (NL); Arie De Rijke, Echt (NL)

(73) Assignee: GEORGIA-PACIFIC LLC, Atlanta, GA (US)

( * ) Notice: Subject to any disclaimer, the term of this patent is extended or adjusted under 35 U.S.C. 154(b) by 778 days.

(21) Appl. No.: 14/890,475

(22) PCT Filed: May 15, 2014

(86) PCT No.: PCT/EP2014/059919
§ 371 (c)(1),
(2) Date: Nov. 11, 2015

(87) PCT Pub. No.: WO2014/184281
PCT Pub. Date: Nov. 20, 2014

(65) Prior Publication Data
US 2016/0107975 A1    Apr. 21, 2016

(30) Foreign Application Priority Data

May 16, 2013 (EP) ..................... 13168030
Sep. 30, 2013 (EP) ..................... 13186708
Oct. 11, 2013 (EP) ..................... 13188263

(51) Int. Cl.
| | |
|---|---|
| B01D 3/36 | (2006.01) |
| C07C 53/02 | (2006.01) |
| C07C 51/42 | (2006.01) |
| C07C 51/44 | (2006.01) |
| C07C 51/46 | (2006.01) |
| C07C 51/48 | (2006.01) |

(52) U.S. Cl.
CPC ............ C07C 51/46 (2013.01); B01D 3/36 (2013.01); *C07C 51/42* (2013.01); *C07C 51/44* (2013.01); *C07C 51/48* (2013.01); *C07C 53/02* (2013.01)

(58) Field of Classification Search
CPC ......... B01D 3/36; C07C 53/02; C07C 43/115; C07C 43/02; C07C 43/18; C07C 51/42; C07C 51/44; C07C 51/46; C07D 307/06
See application file for complete search history.

(56) References Cited

U.S. PATENT DOCUMENTS

| | | | | |
|---|---|---|---|---|
| 1,896,100 | A * | 2/1933 | Ricard | C07C 51/46 203/15 |
| 2,437,519 | A * | 3/1948 | Guinot | C07C 51/46 203/15 |
| 3,983,010 | A * | 9/1976 | Rauch | C07C 51/44 203/15 |
| 5,173,156 | A * | 12/1992 | Berg | B01D 3/40 203/15 |
| 5,608,105 | A | 3/1997 | Fitzpatrick | |
| 8,138,371 | B2 | 3/2012 | Fitzpatrick | |
| 9,073,847 | B2 * | 7/2015 | Tirronen | C07D 307/48 |
| 2014/0275581 | A1 * | 9/2014 | Tirronen | C07C 51/48 549/490 |

FOREIGN PATENT DOCUMENTS

| | | |
|---|---|---|
| WO | 2009130386 A1 | 10/2009 |
| WO | 2013064751 A1 | 5/2013 |

OTHER PUBLICATIONS

International Search Report from corresponding PCT/EP2014/059919, dated Jul. 30, 2014.
Julka et al., "Seelectiong entrainers for azeotriopic distillation", American Institute of Chemical Engineers, vol. 19, 2009, pp. 47-53, XP002712679.
Penn Speciality Chemicals, "methyltetrahydrofuran", Jan. 1, 2005, Jan. 1, 2005, pp. 1-8, XP003028319.

* cited by examiner

*Primary Examiner* — Jonathan Miller
*Assistant Examiner* — Jonathan Luke Pilcher
(74) *Attorney, Agent, or Firm* — Edmonds & Cmaidalka, P.C.; Jared E. Cmaidalka; Ram W. Sabnis

(57) ABSTRACT

The invention relates to a process to separate formic acid from methyltetrahydrofuran (MTHF) said process comprising subjecting a composition comprising formic acid and MTHF to distillation, characterized in that the process comprises adding water to said distillation. This allows for cost-efficient recovery and recycling of MTHF, for example in process to produce and recover formic acid from a biomass hydrolysate.

17 Claims, No Drawings

PROCESS FOR THE SEPARATION OF FORMIC ACID FROM METHYLTETRAHYDROFURAN

CROSS REFERENCE TO RELATED APPLICATIONS

This application is a § 371 National Stage Application of PCT/EP2014/059919, filed 15 May 2014, which claims priority to EP 13168030.8, filed 16 May 2013, EP 13186708.7, filed 30 Sep. 2013, and EP 13188263.1, filed 11 Oct. 2013.

BACKGROUND

Field of the Invention

The invention relates to a process to separate formic acid from methyltetrahydrofuran.

Formic acid is a so-called platform molecule which is used in textile dying, anti-bacterial and as a disinfectant, lime scale remover, leather tanning, silage additive, or preservative, to name a few.

Description of Related Art

Formic acid can be produced from biomass by acid hydrolysis. Examples of such process are described in U.S. Pat. Nos. 8,138,371 and 5,608,105, respectively.

In the production of formic acid from biomass, the acid hydrolysis step is followed by a separation train. This can include extraction and distillation. For example, U.S. Pat. No. 8,138,371 describes the isolation of formic acid from a biomass hydrolysate by vapor condensation. WO2009/130386 discloses a process for the recovery of formic acid involving extraction using octanol and tris-2-ethylhexyl-phosphate as extraction solvent.

The inventors have realized that methyltetrahydrofuran (MTHF) is an excellent solvent to extract formic acid from a biomass hydrolysate. For economic reasons, it is preferred that the MTHF be recovered in order to be recycled to the extraction, and that formic acid and levulinic acid be recovered as valuable products. However, when the inventors tried to separate formic acid and MTHF by distillation, they found that an MTHF-formic acid azeotrope had been formed. Azeotropes can usually be broken by a series of distillations but this involves high energy and equipment cost.

SUMMARY

It is an aim of the invention to recover MTHF from formic acid.

Therefore, in a first aspect the invention provides a process to separate formic acid from MTHF, said process comprising subjecting a composition comprising formic acid and MTHF to distillation, characterized in that the process comprises adding water to said distillation.

The water can be added to the distillation together with (as part of) the composition; for example, water can be added to the composition prior to feeding said composition to the distillation. However, care must be taken that adding water to the composition does not result in the formation of a biphasic solution. It is important that the composition is a monophasic solution prior to distillation. If it is preferred that water is to be added as part of the composition, the skilled person can simply perform a lab or pilot experiment in order to determine the maximal amount of water that can be added to the composition such that the composition still assumes a monophasic solution.

Alternatively, water can be added to the distillation separately from the composition, that is, the water and the composition are added to the distillation separately. Preferably water is added at the top of the distillation, even more preferably by reflux.

DETAILED DESCRIPTION OF A PREFERRED EMBODIMENT

The composition may comprise a formic acid-MTHF azeotrope. That is, at least part of the formic acid in the composition may form an azeotrope with at least part of the MTHF in the composition. Therefore, the invention also provides a process to separate MTHF from a formic acid-MTHF azeotrope, comprising subjecting said formic acid-MTHF azeotrope to distillation, characterized in that the process comprises adding water to said distillation.

The distillation may be any regular column type distillation, suitable to separate high boilers from compounds with lower boiling points.

The amount of water to be added to the distillation is preferably at least the amount needed to form a water-MTHF azeotrope and a water-formic acid azeotrope. The ratio of the different components in azeotropes are known in the art, and it is known that this may be dependent on the temperature, and thus also on the pressure. For example, an MTHF-formic acid azeotrope at 0.5 bar (=80° C.) contains 43 wt % MTHF (the remainder being formic acid); likewise, a formic acid-water azeotrope at 1 bar (=100.8° C.) contains 22.6 wt % water; and an MTHF-water azeotrope at 1 bar (=71° C.) contains 10.6 wt % water. Thus, the skilled person, knowing the amounts of formic acid and MTHF in the composition prior to distillation, can easily calculate a suitable amount of water to be added to the distillation. The upper limit is less critical, but the amount of water is preferably not much greater than needed to form a water-MTHF azeotrope and a water-formic acid azeotrope, as adding too much water may result in enhanced energy consumption making the process less economical.

The amount of water that is added to the distillation is preferably at least 6 wt %, more preferably at least 7 wt %, at least 8 wt %, at least 9 wt %, at least 10 wt %, at least 11 wt %, at least 12 wt %, at least 13 wt %, at least 14 wt %, at least 15 wt %, at least 16 wt %, at least 17 wt %, at least 18 wt %, at least 19 wt %, at least 20 wt %, at least 21 wt %, at least 22 wt %, at least 23 wt %, at least 24 wt %, at least 25 wt %, at least 26 wt %, at least 27 wt %, at least 28 wt %, at least 29 wt %, at least 30 wt %, at least 31 wt %, at least 32 wt %, at least 33 wt %, at least 34 wt %, at least 35 wt %, at least 36 wt %, at least 37 wt %, at least 38 wt %, at least 39 wt %, even more preferably at least 40 wt %, all based on the total weight of the composition which is added to the distillation.

The upper limit is less critical, but the amount of water is preferably not much greater than needed to form a water-MTHF azeotrope and a water-formic acid azeotrope, as adding too much water may result in enhanced energy consumption making the process less economical.

The amount of water that is added to the distillation is preferably 60 wt % or less, more preferably 59 wt % or less, 58 wt % or less, 57 wt % or less, 56 wt % or less, 55 wt % or less, 54 wt % or less, 53 wt % or less, 52 wt % or less, 51 wt % or less, 50 wt % or less, 49 wt % or less, 48 wt % or less, 47 wt % or less, 46 wt % or less, 45 wt % or less, 44 wt % or less, 43 wt % or less, 42 wt % or less, 41 wt % or less, 40 wt % or less, 39 wt % or less, 38 wt % or less, 37 wt % or less, 36 wt % or less, 35 wt % or less, 34 wt % or less, 33 wt % or less, 32 wt % or less, 31 wt % or less, 30 wt % or less, 29 wt % or less, 28 wt % or less, 27 wt % or less, 26 wt % or less, 25 wt % or less, 24 wt % or less, 23 wt % or less, 22 wt % or less, 21 wt % or less, even more preferably 20 wt % or less, all relative to the total weight of the composition which is added to the distillation.

Suitable amounts of water range between 6 and 60 wt %, between 7 and 60 wt %, between 8 and 60 wt %, between 9 and 60 wt %, between 10 and 60 wt %, between 11 and 60 wt %, between 12 and 60 wt %, between 13 and 60 wt %, between 14 and 60 wt %, between 15 and 60 wt %, between 16 and 60 wt %, between 18 and 60 wt %, between 20 and 60 wt %, between 22 and 60 wt %, between 24 and 60 wt %, between 26 and 60 wt %, between 28 and 60 wt %, or between 30 and 60 wt %; or between 6 and 50 wt %, between 7 and 50 wt %, between 8 and 50 wt %, between 9 and 50 wt %, between 10 and 50 wt %, between 11 and 50 wt %, between 12 and 50 wt %, between 13 and 50 wt %, between 14 and 50 wt %, between 15 and 50 wt %, between 16 and 50 wt %, between 18 and 50 wt %, between 20 and 50 wt %, between 22 and 50 wt %, between 24 and 50 wt %, between 26 and 50 wt %, between 28 and 50 wt %, or between 30 and 50 wt %; or between 6 and 40 wt %, between 7 and 40 wt %, between 8 and 40 wt %, between 9 and 40 wt %, between 10 and 40 wt %, between 11 and 40 wt %, between 12 and 40 wt %, between 13 and 40 wt %, between 14 and 40 wt %, between 15 and 40 wt %, between 16 and 40 wt %, between 18 and 40 wt %, between 20 and 40 wt %, between 22 and 40 wt %, between 24 and 40 wt %, between 26 and 40 wt %, between 28 and 40 wt %, or between 30 and 40 wt %; or between 6 and 35 wt %, between 7 and 35 wt %, between 8 and 35 wt %, between 9 and 35 wt %, between 10 and 35 wt %, between 11 and 35 wt %, between 12 and 35 wt %, between 13 and 35 wt %, between 14 and 35 wt %, between 15 and 35 wt %, between 16 and 35 wt %, between 18 and 35 wt %, between 20 and 35 wt %, between 22 and 35 wt %, between 24 and 35 wt %, between 26 and 35 wt %, between 28 and 35 wt %, between 30 and 35 wt %; or between or between 6 and 30 wt %, between 7 and 30 wt %, between 8 and 30 wt %, between 9 and 30 wt %, between 10 and 30 wt %, between 11 and 30 wt %, between 12 and 30 wt %, between 13 and 30 wt %, between 14 and 30 wt %, between 15 and 30 wt %, between 16 and 30 wt %, between 18 and 30 wt %, between 20 and 30 wt %, between 22 and 30 wt %, between 24 and 30 wt %, between 26 and 30 wt %, between 28 and 30 wt %, or between 30 and 40 wt %, all relative to the total weight of the composition which is added to the distillation.

The temperature of the distillation is not critical, and may depend on the applied pressure. At atmospheric pressure the temperature at the head of the column may range from 60° C. to 100° C., more preferably between 70° C. and 80° C., which is the temperature range of the MTHF-water azeotropic boiling point.

The composition preferably also comprises levulinic acid. Levulinic acid is a starting molecule for the synthesis of esters known as fuel additive and is known to be useful as plasticisers and solvents. Levulinic acid can be used to synthesize MTHF or can be used as a solvent. Other applications of levulinic acid are for example the synthesis of delta-amino levulinic acid used as herbicides and pesticides, diphenolic acid used to synthesize polycarbonates and succinic acid used to make polyesters. Levulinic acid can also be used to produce gamma-valerolactone (5-methylbutyrolactone), which in turn can be used for production of adipic acid (1,6-hexanedioic acid). In the production of levulinic acid from biomass, formic acid is produced as a by-product, and vice versa. Other possible components in the composition are acetic acid and/or furfural.

In an embodiment the process includes recovering MTHF as a distillate and recovering formic acid as a distillation residue. The recovered MTHF may be in the form of a water-MTHF azeotrope. The process may further comprise isolating the MTHF from said water-MTHF azeotrope. The recovered MTHF may be recycled to an extraction step.

In an embodiment, the recovered formic acid is in the form of a water-formic acid azeotrope. The process may comprise isolating the formic acid from said water-formic acid azeotrope.

In an embodiment, the composition comprises an organic phase obtained by extraction. Extraction takes advantage of differences in the chemical properties of the feed components, such as differences in polarity and hydrophobic/hydrophilic character to separate them (T. C. Frank, L. Dahuron, B. S. Holden, W. D. Prince, A. F. Seibert, L. C. Wilson, Liquid-liquid extraction and other liquid-liquid operations and equipment in Perry's Chemical Engineering Handbook, 8th Edition, Section 15). In the context of the invention, "extraction", "solvent extraction", and "solvent-solvent extraction" are understood to be the same. In the process of the invention extraction may be used to separate formic acid and preferably levulinic acid and optionally other components from an aqueous composition which is preferably a biomass hydrolysate using MTHF as a solvent. The extraction yields an aqueous phase and an organic phase. The solvent in the extraction may comprise other solvents in addition to MTHF. MTHF advantageously gives excellent extraction of formic acid and preferably levulinic acid. The extraction yields an organic phase and an aqueous phase. The organic phase comprises MTHF and formic acid, and preferably also levulinic acid, acetic acid, furfural, and/or humins.

The composition may comprise humins. A problem associated with the production of bio-based products such as levulinic acid and formic acid by acid hydrolysis of biomass is formation of tar or humins, which can be produced in amounts up to 10 to 50% w/w of the total reaction mixture, creating a high overall purification and separation effort. Tar and char represent organic material which is insoluble in water, which is dark in colour and which tends to become viscous and very dark to almost black when concentrated. Tar can be formed during heating of organic material, for example by pyrolysis, but is also formed when carbohydrates are subjected to acid hydrolysis, particularly when done at high temperatures. Char usually refers to solid material, for example the remains of solid biomass that has been incompletely combusted, such as charcoal if wood is incompletely burned. Tar usually refers (viscous) liquid, e.g. derived from the destructive distillation of organic matter. The presence of tar is undesired for a number of reasons. Firstly, its dark colour makes the product unattractive from the perspective of the user or customer. Secondly, the tar may negatively affect the performance of the bio-based product in the application. For this reason tar is preferably removed from the desired product. Yang and Sen (Chem. Sus. Chem. 2010, vol. 3, 597-603) report the formation of humins during production of fuels from carbohydrates such as fructose. They speculate that the humins are formed by acid-catalyzed dehydration. According to U.S. Pat. No. 7,896,944 the molecular weight of humins ranges from 2.5 to 300 kDa.

The extraction may comprise contacting MTHF with a biomass hydrolysate to yield an organic phase comprising MTHF and formic acid, and an aqueous phase, and recovering the organic phase. Said organic phase may correspond to the composition comprising formic acid and MTHF. Such a biomass hydrolysate may be obtained by (preferably acid) hydrolysis under conditions such that it results in the formation of levulinic acid. Suitable acids for acid hydrolysis of biomass include sulphuric acid, hydrochloric acid, and phosphoric acid.

The biomass may be or may be derived from wood, grass, cereal, starch, algae, tree bark, hay, straw, leaves, paper pulp, paper sludge, or dung. Paper pulp, or simply pulp, is a lignocellulosic fibrous material prepared by chemically or mechanically separating cellulose from wood, fibre crops or waste paper. Pulp is rich in cellulose and other carbohydrates. Paper sludge, or simply sludge, is a lignocellulosic fibrous containing cellulose fibres too short for usage in the paper industry. The biomass may comprise lignocellulosic biomass. Lignocellulosic biomass typically has a fibrous nature and comprises a bran fraction that contains the majority of lignocellulosic (bran) fibers. As an example, corn fiber is a heterogeneous complex of carbohydrate polymers and lignin. It is primarily composed of the outer kernel covering or seed pericarp, along with 10-25% adherent starch. Carbohydrate analyses of corn fiber vary considerably according to the source of the material. The lignocellulosic biomass may comprise hemicellulose.

In a preferred embodiment, the biomass hydrolysate is made by acid hydrolysis of C6 sugars, particularly fructose, glucose, or mixtures thereof. Sucrose ($C_{12}H_{22}O_{11}$) can be broken down into one molecule of glucose ($C_6H_{12}O_6$) plus one molecule of fructose (also $C_6H_{12}O_6$, an isomer of glucose), in a weakly acidic environment by a process called inversion. Fructose can also be made by enzymatic isomerization of glucose. Sucrose is commonly produced from biomass such as beet, corn and cane. Thus, within the context of the invention, glucose and fructose are biomass-derived.

Suitable reaction conditions for the acid hydrolysis of biomass or biomass-derived compounds are known in the art.

The process may comprise multiple distillation steps. The composition may be a distillate or distillation residue from a preceding distillation step.

In an embodiment a mixture comprising MTHF, formic acid and optionally at least one other compound selected from levulinic acid, acetic acid, furfural, and humins, preferably an organic phase obtained from a solvent-extraction step, is subjected to a first distillation, yielding a first distillate comprising MTHF and water (e.g. as top fraction), and a first distillation residue comprising MTHF, formic acid and optionally the at least one other compound; whereby said distillation residue is subjected to a second distillation yielding a second distillate comprising MTHF and formic acid, which second distillate may correspond to the composition of the process of the invention and which is optionally in the form of an azeotrope, and a second distillation residue optionally comprising the at least one other compound; said second distillate is subjected to a third distillation, whereby water is added to said third distillation, in order to separate the MTHF from the formic acid. This third distillation yields a third distillate comprising MTHF and water, optionally in the form of an azeotrope, and a third distillation residue comprising formic acid and water, optionally in the form of an azeotrope. Any MTHF-water azeotrope and formic acid-water azeotrope may be separated by methods known in the art. The MTHF in the first distillate and the third distillate may be recovered and recycled to an extraction. The ratio of MTHF to formic acid in this embodiment is preferably around 1:2.

In another embodiment the composition of the process of the invention, optionally comprising at least one other compound selected from levulinic acid, acetic acid, furfural, and humins, preferably an organic phase obtained from a solvent-extraction step, is subjected to a first distillation, whereby water is added to said first distillation; this first distillation yields a first distillate comprising MTHF and water, optionally in the form of azeotrope, and a first distillation residue comprising formic acid and optionally at least one other compound. The MTHF in the first distillate may be recovered and recycled to an extraction. The first distillation residue may be discarded, or it may be subjected to a second distillation to yield a second distillate comprising water and formic acid and optionally acetic acid, and a second distillation residue comprising heavy compounds such as levulinic acid and humins. In order to recover levulinic acid, the second distillation residue can be subjected to a third distillation and levulinic acid can be recovered as a third distillate.

The process has several advantages. Firstly, the use of MTHF as extraction solvent allows for the efficient separation and recovery of formic acid and levulinic acid from a biomass hydrolysate. Secondly, adding water to a distillation allows for cost-efficient recovery and recycling of MTHF.

EXAMPLES

Example 1

A solution (total weight: 204.71 g) containing 51.5% formic acid, 34.3% MTHF and 14.2% water was subjected to split column batch distillation at atmospheric pressure. During the distillation 12 fractions were isolated and analysed whereby fraction 12 represents the distillation residue. Table 1 shows the composition of the fractions and the representative weight of the total intake of the mixture.

TABLE 1

Distillation results

| fraction | amount (g) | formic acid (wt %) | MTHF (wt %) | water (wt %) |
|---|---|---|---|---|
| 1-6 | 72.1 | <0.01 | 93.3 | 9.7 |
| 7 | 2.63 | 7 | 82.8 | 12.5 |
| 8 | 5.14 | 78.7 | 20.9 | 1.2 |
| 9 | 10.10 | 90.3 | 8.9 | 0.8 |
| 10 | 14.51 | 87.7 | 0.77 | 11.5 |
| 11 | 7.46 | 83.0 | <0.01 | 17.0 |
| 12 | 91.00 | 77.5 | <0.01 | 22.5 |
| mass recovered | 202.93 | | | |

The mass balance is at least 99% which indicates that there are no losses of material during the distillation and no by product formation.

From this data it is evident that the distillation can be conducted in a continuous manner yielding formic acid essentially free of MTHF and an MTHF fraction essentially free of formic acid.

Example 2

A solution (total weight: 200.8 g) containing 57.0% formic acid, 38.0% MTHF and 5.0% water was subjected to split column batch distillation at atmospheric pressure. During the distillation in total 18 fractions were isolated and analysed whereby fraction 18 represents the distillation residue. Table 2 shows the composition of the fractions and the representative weight of the total intake of the solution.

TABLE 2

Distillation results

| fraction | amount (g) | formic acid (wt %) | MTHF (wt %) | water (wt %) |
|---|---|---|---|---|
| 1-4 | 27.84 | 0.004 | 89.3 | 10.6 |
| 5-9 | 13.17 | 0.028 | 89.3 | 10.6 |
| 10-11 | 10.77 | 47.8 | 50.6 | 4.6 |
| 12-13 | 50.70 | 45.6 | 42.1 | 2.3 |
| 14-15 | 44.85 | 70.3 | 28.5 | 1.2 |
| 16 | 19.77 | 91.3 | 8.1 | 0.6 |
| 17 | 7.21 | 86.2 | 0.7 | 13.1 |
| 18 | 22.49 | 79.2 | 0.02 | 20.6 |
| mass recovered | 196.80 | | | |

The mass balance is at least 98% which indicates that there are no losses of material during the distillation and no by product formation.

Example 3

A solution containing 60% formic acid and 40% MTHF is subjected to split column batch distillation at atmospheric pressure. Distillation fractions and the residue are isolated and analysed. The mass balance indicates that are no losses of material during the distillation and no by product formation. However, the MTHF and formic acid cannot be separated from each other. A formic acid-MTHF azeotrope is demonstrated at 80° C. and 0.5 bar.

The invention claimed is:

1. A process for separating formic acid from methyltetrahydrofuran, comprising:
   subjecting a composition comprising formic acid and methyltetrahydrofuran to distillation, wherein the composition comprises a formic acid-methyltetrahydrofuran azeotrope;
   adding water to the distillation in an amount sufficient to form a water-methyltetrahydrofuran azeotrope and a water-formic acid azeotrope;
   recovering methyltetrahydrofuran as a distillate; and
   recovering formic acid as a distillation residue, wherein the recovered formic acid is in the form of a water-formic acid azeotrope.

2. The process according to claim 1, wherein the amount of water added to the distillation is at least 14 wt % to 60 wt %, based on a total weight of the composition.

3. The process according to claim 1, wherein the amount of water added to the distillation is at least 6 wt % based on a total weight of the composition.

4. The process according to claim 1, wherein the water is added by reflux.

5. The process according to claim 1, wherein the recovered methyltetrahydrofuran is in the form of a water-methyltetrahydrofuran azeotrope.

6. The process according to claim 5, further comprising isolating the methyltetrahydrofuran from the water-methyltetrahydrofuran azeotrope.

7. The process according to claim 1, further comprising isolating the formic acid from the water-formic acid azeotrope.

8. The process according to claim 1, wherein the composition comprises an organic phase obtained by extraction.

9. The process according to claim 8, wherein the extraction comprises contacting methyltetrahydrofuran with a biomass hydrolysate.

10. The process according to claim 1, wherein the composition is a distillate.

11. The process according to claim 1, further comprising feeding the recovered methyltetrahydrofuran to an extraction.

12. A process for separating formic acid from methyltetrahydrofuran, comprising:
    distilling a composition comprising formic acid, methyltetrahydrofuran, and a formic acid-methyltetrahydrofuran azeotrope;
    adding water during distillation of the composition in an amount sufficient to form a water-methyltetrahydrofuran azeotrope and a water-formic acid azeotrope;
    recovering formic acid as a distillation residue in the form of a recovered formic acid is in the form of a water-formic acid azeotrope; and
    isolating the formic acid from the water-formic acid azeotrope.

13. The process according to claim 12, wherein the amount of water added during distillation of the composition is at least 6 wt % to 60 wt %, based on a total weight of the composition.

14. The process according to claim 12, wherein the amount of water added to the distillation is at least 14 wt % to 60 wt %, based on a total weight of the composition.

15. The process according to claim 12, wherein the composition further comprises levulinic acid, humins, or a mixture thereof.

16. A process for separating formic acid from methyltetrahydrofuran, comprising:
    distilling a composition comprising formic acid, methyltetrahydrofuran, and a formic acid-methyltetrahydrofuran azeotrope;
    adding water during distillation of the composition in an amount sufficient to form a water-methyltetrahydrofuran azeotrope and a water-formic acid azeotrope;
    recovering methyltetrahydrofuran as a distillate in the form of a water-methyltetrahydrofuran azeotrope; and
    recovering formic acid as a distillation residue in the form of a water-formic acid azeotrope.

17. The process of claim 16, further comprising:
    isolating the methyltetrahydrofuran from the water methyltetrahydrofuran azeotrope; and
    isolating the formic acid from the water-formic acid azeotrope.

* * * * *